United States Patent [19]

Raetz et al.

[11] Patent Number: 4,918,061
[45] Date of Patent: Apr. 17, 1990

[54] METHOD OF PREVENTING DISEASES CAUSED BY GRAM-NEGATIVE ENDOTOXIN IN MAMMALS

[75] Inventors: Christian R. H. Raetz, Middleton; Richard A. Proctor, Madison; James A. Will, Columbus, all of Wis.

[73] Assignee: Wisconsin Alumni Research Foundation, Madison, Wis.

[21] Appl. No.: 206,994

[22] Filed: Jun. 8, 1988

Related U.S. Application Data

[63] Continuation of Ser. No. 719,328, Apr. 3, 1985, abandoned, which is a continuation-in-part of Ser. No. 492,378, May 6, 1983, abandoned.

[51] Int. Cl.$^4$ ............................................. A61K 31/70
[52] U.S. Cl. ...................................................... 514/62
[58] Field of Search ............................. 514/53, 54, 62

[56] References Cited

PUBLICATIONS

Chemical Abstracts 87:129203u (1977).
Chemical Abstracts 88:165751a (1978).
Chemical Abstracts 93:39049t (1980).
Raetz, C. R. H., Purcell, S., and Takayama, K. (1983), Proc. Natl. Acad. Sci. USA, 80, 4624–4628.
Weinberg, J. B., Chapman, H. A., Jr., and Hibbs, J. B., Jr. (1978), J. Immunol. 121, 72–80.
Ribi, E. E., Granger, D. L., Milner, K. C., and Strain, S. M. (1975) J. Natl. Cancer Ins. 55, 1253–1257.
Ribi, E. E., Cantrell, J. L., Von Eschen, K. B., and Schwartzman, S. (1979) Cancer Res. 39, 4756–4759.
Snapper, J. R., Bernard, G. R., Hinson, J. M., Jr., Hutchinson, A. A. Loyd, J. E., Ogletree, M. L. and Brigham, K. L. (1983) Am. Rev. Respir. Dis. 127, 306–309.
Brigham, K. L., Bowers, R. E., and Haynes, J. (1979), Cir. Res. 45(2), 292–297.
Kashtan, J., Blaisdell, F. W., Lin, H. J., and Zaiss, C. (1982) Adv. Schock Res. 7, 173–177.
Galanos, C., Rietschel, E. Th., Luderitz, O., Westphal, O., Kim, Y. B., and Watson, D. W., (1972) Eur. J. Biochem. 31, 230–233.
Takayama, K., Qureshi, N., Mascagni, P., Nashed, M. A., Anderson, L., and Raetz, C. R. H. (1983) J. Biol. Chem. 258, 7379–7385.
Raetz, C. R. H. (1984) Rev. Infect. Dis. 6, 463–471.
Bulawa, C. E., and Raetz, C. R. H. (1984) J. Biol. Chem. 259, 4846–4851.
Ray, B. L., Painter, G., and Raetz, C. R. H. (1984) J. Biol. Chem. 259, 4852–4859.
Wightman, P. D., and Raetz, C. R. H. (1984) J. Biol. Chem. 259, 10048–10052.
Takayama, K., Qureshi, N., Raetz, C. R. H., Ribi, E., Peterson, J., Cantrell, J. L., Pearson, F. C., Wiggins, J., and Johnson, A. G. (1984) Infect. Immun. 45, 350–355.

Primary Examiner—Jerome D. Goldberg
Attorney, Agent, or Firm—Quarles & Brady

[57] ABSTRACT

A method of treating animals to protect them from the toxic effects of gram-negative endotoxin comprises administering to said animals a safe and effective amount of a compound having lipid X activity.

1 Claim, 4 Drawing Sheets

METHOD OF PREVENTING DISEASES CAUSED BY GRAM-NEGATIVE ENDOTOXIN IN MAMMALS

RELATED CASE

This application is a continuation of application Ser. No. 719,328 filed Apr. 3, 1985, which is a continuation-in-part of Ser. No. 492,378, filed May 6, 1983, both now abandoned.

FIELD OF THE INVENTION

This invention relates to a method for treating mammals so as to prevent clinical complications and death arising from the presence of gram-negative endotoxin (lipopolysaccharide) in their bodies, by administering to mammals a compound having lipid X activity in an amount sufficient to induce said protection.

BACKGROUND OF THE INVENTION

Lipopolysaccharide (LPS) is a major constituent of the outer membranes of gram-negative bacteria. Structural studies have shown that it consist of the following three distinct domains: 1) the O-antigen region, which is a strain-specific polysaccharide moiety and determines the antigenic speificity of the organism; 2) the core region, which is relatively conserved with respect to its sugar composition and may play a role in maintaining the integrity of the outer membrane; and 3) the lipid A region, which is also conserved and functions as a hydrophobic anchor holding lipopolysaccharide in place. The lipid A portion of lipopolysaccharide constitutes most of the outer monolayer of the outer membrane in gram-negatives.

Lipopolysaccharide is known to trigger many pathophysiological events in mammals, either when it is injected or when it accumulates due to gram-negative infection. In general, the hydrophobic lipid A moiety is responsible for these pathophysiolocical effects, which tend to be either immunostimulatory or toxic. In the former category there are events such as B-lymphocyte mitogenesis (1), macrophage activation (2), and the induction of tumor necrosis in certain experimental systems (3). In the latter (toxic) category there are responses such as peripheral vascular collapse ("endotoxic" shock) (4), pulmonary hypertension (5), pulmonary edema (6), disseminated intravascular coagulopathy (7) and pyrogenicity (8).

The complex events elicited by lipid A in mammals are not well understood at a molecular level, since the correct covalent structure of lipid A was unknown prior to 1983 (9, 10). The recent application of fast atom bombardment mass spectrometry and NMR spectroscopy to this problem, together with the recent discovery of a simple monosaccharide precursor (9), has led to the following proposed minimal structure of lipid A:

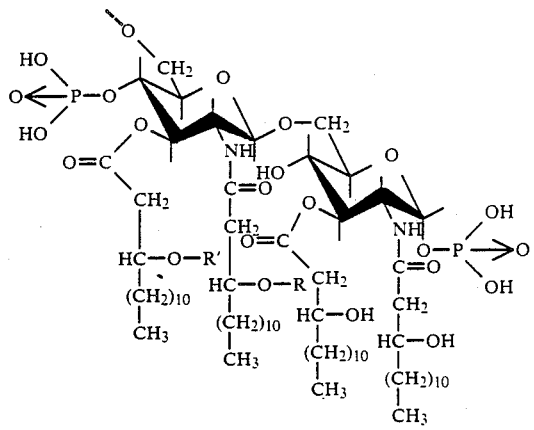

The above general structure of lipid A has been confirmed in *Escherichia coli*, *Salmonella typhimurium* and *Salmonella minnesota*. The discovery of the monosaccharide precursor, lipid X, has also led to the elucidation of the biosynthetic pathway for the formation of lipid A in *E. coli* and *S typhimurium* (11, 12). The availability of these various novel lipid A precursors and substructures has made it possible to dissect the chemical and structural requirements for the numerous biological effects of lipid A.

BRIEF SUMMARY OF THE INVENTION

We have discovered a method of treating mammals to protect them from gram-negative endotoxins which comprises administering to said mammals a safe and effective amount of a compound having lipid X activity. The monosaccharide, lipid X, mimics many of the immunostimulatory effects of lipid A (13), but does not have its extreme toxicity (14).

DESCRIPTION OF PREFERRED EMBODIMENT

Figure 1A:
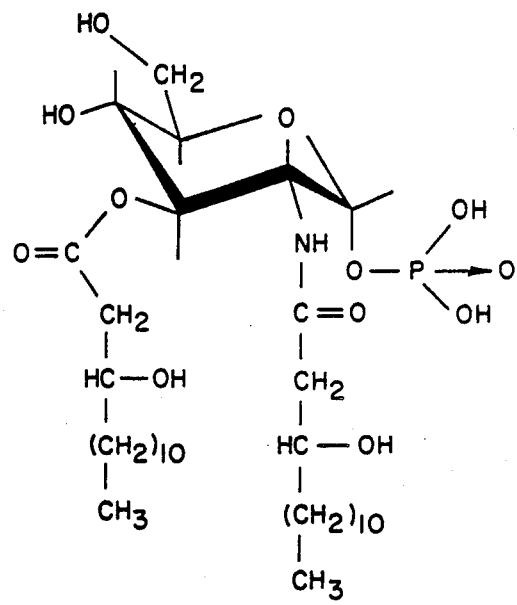
FIG. 1. Shows the covalent structure of lipid X and its relationship to mature lipid A.
Figure 1B:
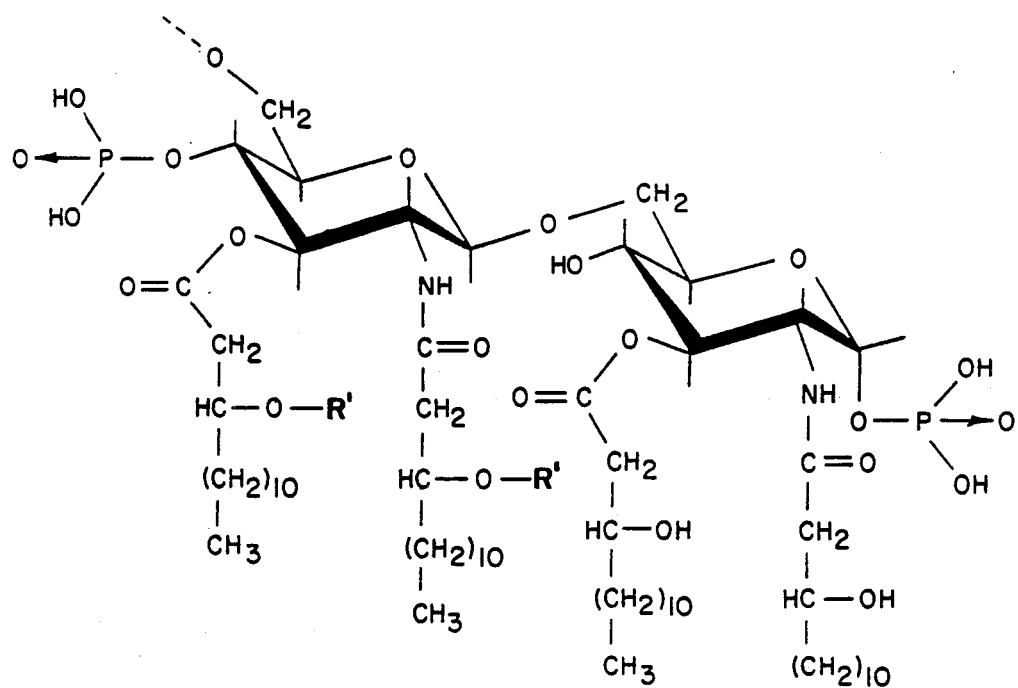
Figure 2:
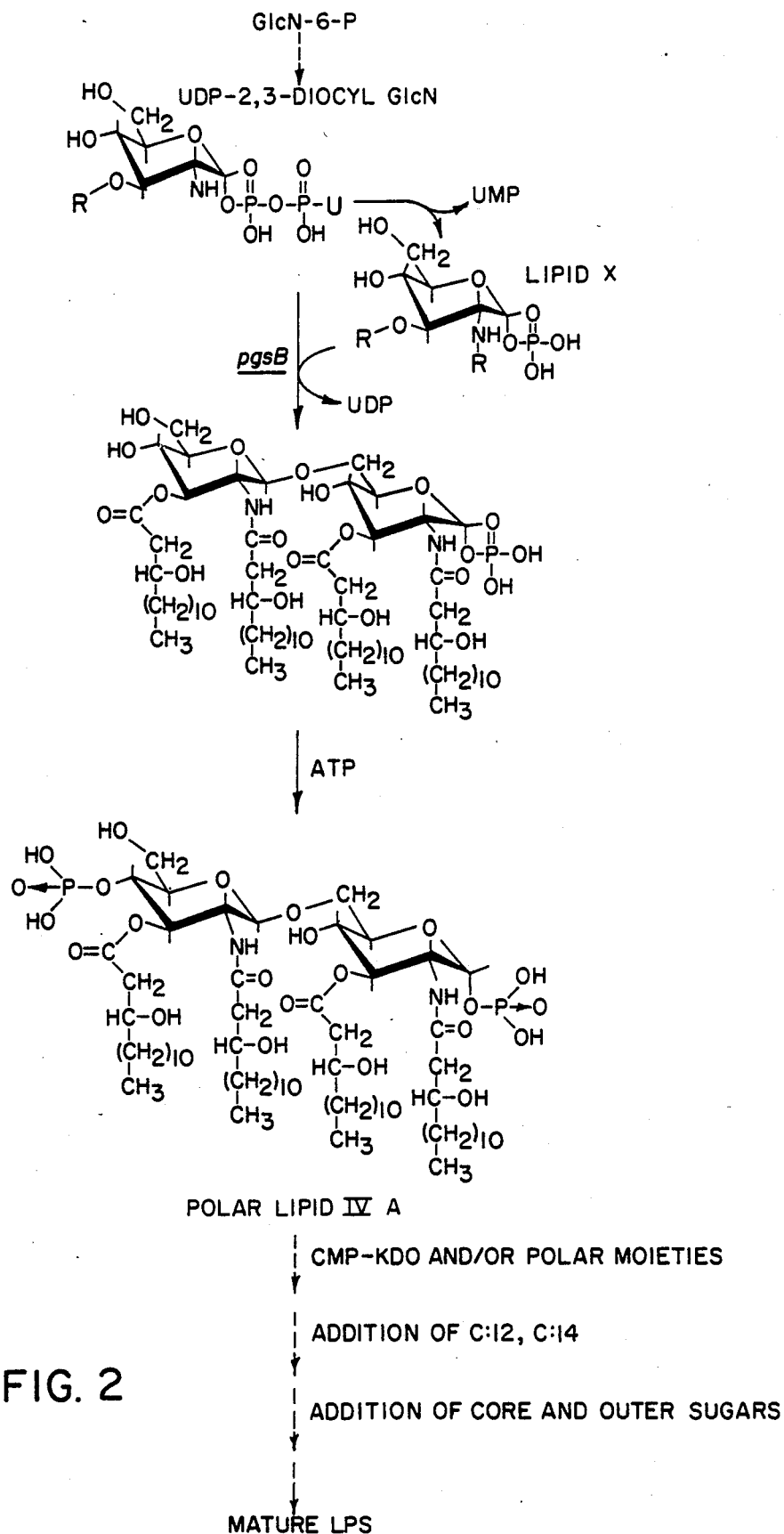
FIG. 2. Diagrams the biosynthesis of lipid A from lipid X.

In the practice of the preferred embodiment the compound, lipid X, is administered to an animal in a safe and effective amount to protect it from the toxic effects of gram-negative endotoxins.

Lipid X is a B cell mitogen which is capable of activating macrophages with release of protaglandin $E_2$, it can activate macrophage protein kinase C (15), and it is capable of inducing regression of experimental tumors in guinea pigs (16). Lipid X may be represented by the following formula:

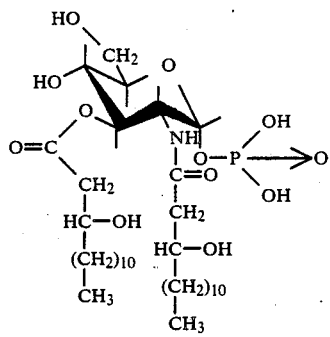

It appears that the ester linked $\beta$-hydroxymyristoyl moiety at position 3 of lipid X is essential for Lipid X biological activity. Removal of this moiety by mild alkali treatment results in the formation of an N-monoacyl glucosamine 1-phosphate that is biologically inert. Removal of the phosphate moiety by mild acid treatment also reduces biological activity, but this may be due to the inherent solubility of dephospho-X.

The question of whether or not lipid X has the "endotoxic" activity of lipopolysaccharide and lipid A has been examined in sheep, which display sensitivity similar to that of man, and in mice (17), which are relatively resistant.

The $LD_{50}$ for the lipopolysaccharide in sheep is about 10–20 $\mu$g/kg (intravenous), while in mice it is about 5 mg/kg. In sheep (and probably also in humans) lipopolysaccharide causes death by triggering pulmonary hypertension, pulmonary edema, and peripheral vascular collapse. Death usually occurs within 8 to 48 hours after injection of lipopolysaccharide or lipid A. Occasionally, death will occur at 1–2 weeks. This is usually the result of disseminated intravascular coagulopathy leading to renal cortical necrosis and uremic death.

The hemodynamic response of sheep to lipid X has been studied (18). Essentially, the conclusions are that: 1) lipid X (40 $\mu$g/kg cumulative dose) causes a transient (3–5 min) increase in pulmonary arterial pressure, that may be attributed to prostaglandin release, or stimulated synthesis. However, unlike endotoxin (i.e. lipopolysaccharide), there is no delay between the injection of lipid X and the increase of pulmonary arterial pressure. Also, the increase in pulmonary blood pressure is much more prolonged with lipopplysaccharide than with lipid X, persisting over several hours. 2) With lipid X, increased permeability of the pulmonary circulation occurs to a very mild degree compared to endotoxin, and life-threatening pulmonary edema does not develop. Even injection of very high doses of lipid X into sheep fails to cause terminal endotoxemia. Injection of as much as 500–1000 $\mu$g/kg of lipid X intravenously in sheep causes a slightly more prolonged pulmonary hypertension (5–10 min) than at 40 $\mu$g/kg (3–5 min), but nevertheless, the episode is very short compared to that following injection of 1–10 $\mu$g/kg of lipopolysaccharide. The only significant symptoms observed after injection of lipid X alone are transient lethargy and shortness of breath (15–30 min), without significant distress or obvious adverse long-term consequences.

We have now discovered that the pretreatment of mammals, such as sheep (19) or mice, with lipid X makes them immediately resistant to the lethal effects of injection of gram-negative endotoxin. This apparent antagonism between lipid X and endotoxin may have useful applications in clinical situations and disease states that are caused by endotoxin, such as gram-negative sepsis following surgery in humans and animals, bovine or porcine mastitis, and other endotoxin-related veterinary diseases listed in Tables I and II.

In addition to Lipid X, there are derivatives of Lipid X that possess lipid X activity (i.e. the ability to protect against gram-negative endo-toxin). Such derivatives possess the essential ester linked $\beta$-hydroxymyristoyl moiety at position 3 but may have substitutents at other positions that do not interfere with lipid X activity.

Representative of such derivatives are compounds of the formula:

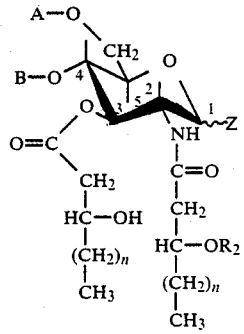

in which the preferred sugar stereochemistry is that of glucosamine; A and B are the same or different, and are H, a hydrocarbon structure, a fatty acyl chain, or another functional group; $R_2$ is a fatty acyl chain, n is an alkyl group of 2 to 24 carbon atoms, and substituent Z is a water solubilizing group.

The invention is further illustrated by the following:

EXPERIMENTAL PROCEDURES AND MATERIALS.

Preparation of E. coli lipid X. The 2,3-diacylglucosamine 1-phosphate (E. coli lipid X) was isolated from E. coli strain MN7 (ATCC #39328) as described previously (9). Lipid X obtained in this manner is a solid white powder. Stock solutions (1–10 mg/ml) are usually prepared in aqueous 1 mM EDTA titrated to pH 8 with Tris-free base. Other monovalent counter ions, such as $(NH_4)^+$, $Na^+$, $K^+$, etc., may also be used, but divalent cations such as $Mg^{++}$ and $Ca^{++}$ cause the lipid to precipitate. In Tris-EDTA at pH 8 the lipid X forms a clear viscous solution, that may be sterilized by filtration without prior sonic irradiation. In experiments involving the use of mice, solid lipid X was first dissolved in 0.9% saline (instead of water) and titrated with Tris-free base to pH 8 in the same manner. Stock solutions of lipid X (5–10 mg/ml) could be stored frozen at −20° C. for many months without evidence of significant deterioration.

Figure 3:
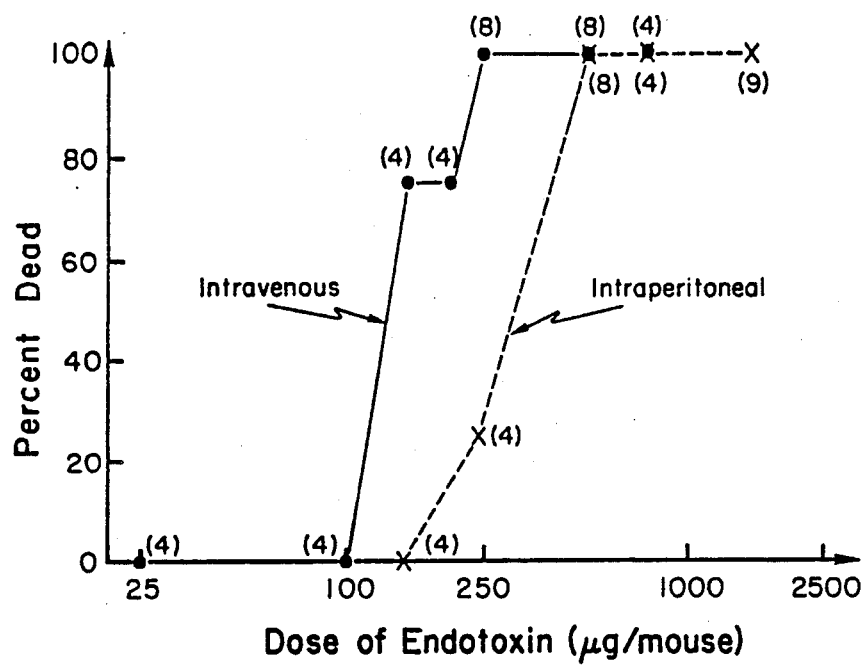
FIG. 3. Shows the dose-response curves for lethal endotoxemia in mice. The lethal dose of *E. coli* 011:B4 endotoxin (Westphal method, Sigma, St. Louis, MO) was determined in 8–10 week old, C57BL/10 mice (Jackson Laboratory, ME) weighing 20–25 gm. Mice were injected either intraperitoneally (x), or they were ether-anesthetized and injected intravenously with a total volume of 0.05–0.2 ml via the retroorbital plexus (o). Endotoxin was dissolved in sterile, phosphate-buffered saline. All deaths occurred within 72 hours of challenge; however, the animals were observed for at least 7 days. The number of animals per group is indicated in parentheses. It is important to generate a dose-response curve like the one shown for each lot of endotoxin and mouse population employed.
Figure 4:
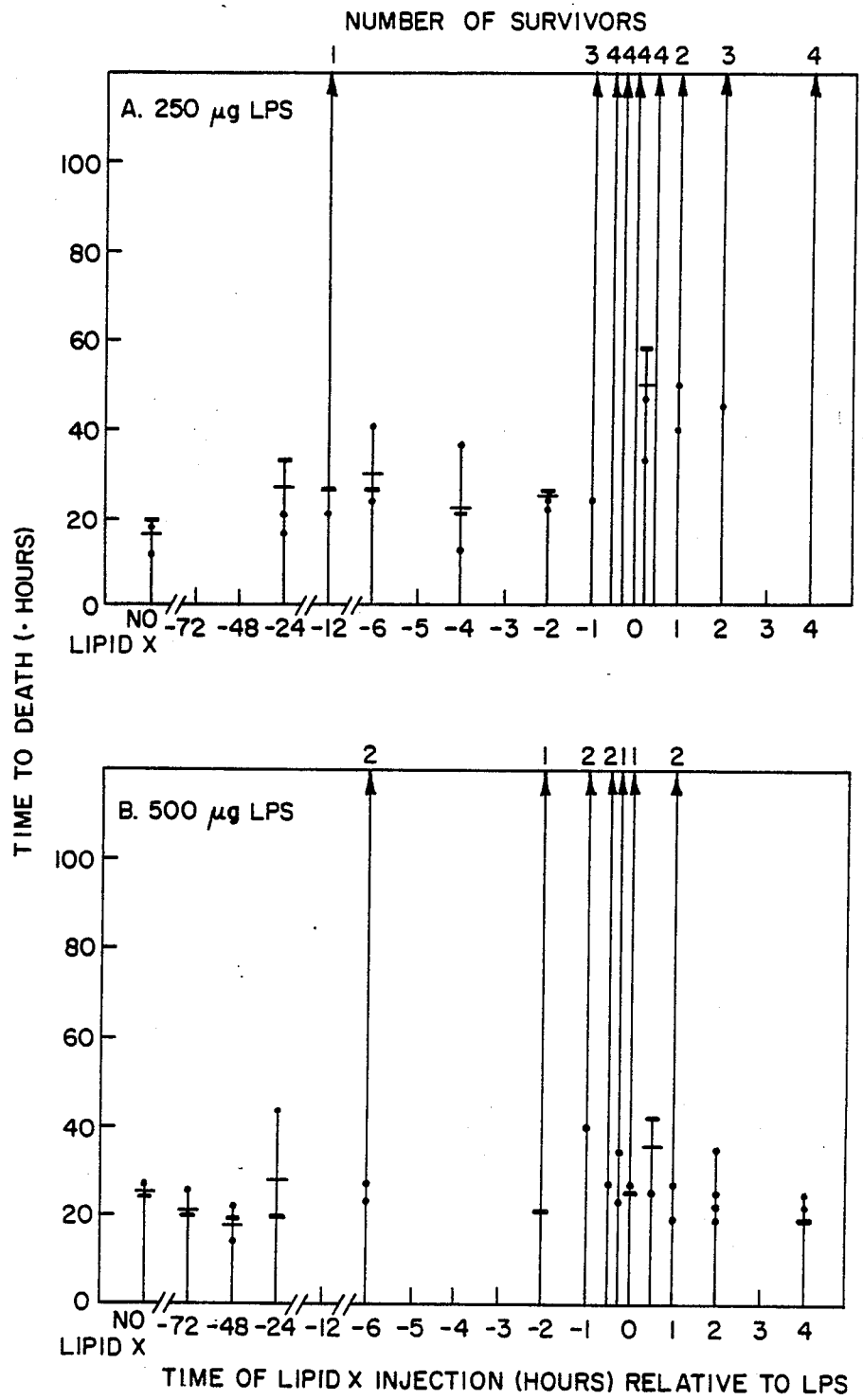
FIG. 4. Shows the protection against lethal endotoxemia provided by lipid X. The times (in hours) that mice were given 750 μg of lipid X intravenously are given relative to the time (designated O) when the challenge dose of endotoxin was given. Mice received either 250 μg (panel A) or 500 μg (panel B) of endotoxin intravenously. Controls receiving no lipid X are shown at the left of each panel. The number of mice per group is either three or four, and is the sum of the dead and the living. The number of survivors is shown at the top of the panel. Each point represents the death of one mouse. When all individuals died the mean time of death is shown as a horizontal bar. No deaths occurred after 5 days. Doses of lipid X were administered in 0.1 ml of physiological saline that had been titrated to pH 8 with Tris to dissolve the lipid.

*Escherichia coli* lipopolysaccharide (sero-type *E. coli* 011:B4) was prepared by the phenol-water method of Westphal (2,3) and obtained from Difco, Detroit, MI. Stock solutions of 5 mg/ml were prepared in sterile 0.9% saline. The $LD_{50}$ of this material in sheep is approximately 10–20 μg/kg when administered intravenously. In mice the $LD_{50}$ is about 5 mg/kg intravenously and about 10 mg/kg injected intraperitoneally. Toxicity data are summarized in FIG. 3.

Experimental Animals. Eight week old mice (strain C57BL/10) were purchased from Jackson Laboratories, Bar Harbor, ME. Mixed bred sheep weighing 30–70 kg were obtained from the University of Wisconsin Experimental Farms. Sheep were prepared as follows: at least 24 hours before each experiment catheters were percutaneously placed in the pulmonary artery. Any other catheterizations that were required for infusion were done at this time. All studies were performed on awake, unrestrained sheep placed in portable stanchions with food and water ad libitum. Electronically calculated pulmonary artery pressures as well as heart rates were recorded at various intervals on a Gilson polygraph (Gilson Instruments, Middleton, WI). To ensure a stable baseline prior to the injection of test compounds, approximately 1 hour of baseline measurements were recorded.

Mice were allowed to rest for at least 7 days following their arrival and were sexually segregated and housed at 5 per cage with food and water ad libitum. Intravenous injection of lipid X (dissolved in saline as described above) and/or lipopolysaccharide was achieved by the retroorbital sinus route using a 27 gauge needle. No more than 0.1 ml of fluid was injected at a time. Just prior to injection, the mice were lightly anesthetized with ether. Following the injection, mice were observed every 0.5–6 hours and the time of death was recorded. In a few experiments, mice were injected by the intraperitoneal route with solutions of lipid X and/or lipopolysaccharide similar to those described above.

RESULTS:

Lipid X protects mice against lethal endotoxemia.

Since lipid X may be considered a substructure of lipid A but appears to be nontoxic, it seemed reasonable to examine the hypothesis that it might act as an endotoxin antagonist. To do a statistically controlled study of the ability of lipid X to prevent lethal endotoxemia, mice were initially employed, despite the inherent drawback that mice are far more resistant to the deleterious effects of lipopolysaccharide than are sheep, cattle or humans.

To test for the toxicity of lipid X in mice, C57BL/10 mice were challenged with 750, 2000 or 5000 μg of lipid X intraperitoneally (12 mice) or with 750, 1500 or 3000 μg intravenously (7 mice). All these mice lived. Consequently, lipid X appeared to be nontoxic in mice, as in sheep. As discussed more fully below, 40 sheep have been injected with lipid X and no serious adverse complications of lipid X administration have been observed so far.

The lethal dose of *E. coli* endotoxin was determined both for the intravenous and of the intraperitoneal challenge. The lethal dose that killed 100% of the mice ($LD_{100}$) was 250 μg intravenously and 500 μg intraperitoneally. (It is important to standardize each lot of endotoxin with each lot of mice.) To determine the approximate dose of lipid X needed to protect against a lethal challenge of endotoxin, mice were pretreated with lipid X intraperitoneally 2 hours before challenge with 1500 μg of endotoxin, which is 3 times the $LD_{100}$ dose. Pretreatment of mice with lipid X appeared to prolong the time to death four-fold (from about 20 hours to 80 hours - data not shown).

However, because both lipid X and lipopolysaccharide (LPS) were given intraperitoneally in these preliminary experiments, the possibility existed of slow or variable rates of absorption. Consequently, an intravenous challenge route was selected to test for protective efficiency. Mice were given 750 μg of lipid X from 24 hours prior to 6 hours after endotoxin challenge with 1–2 $LD_{100}$ doses. Forty-one percent of mice receiving 500 μg lipid X from 6 hours prior to endotoxin challenge through 1 hour after LPS challenge survived. When a lower endotoxin challenge dose (250 μg) was used, 81% of the mice survived if treated with lipid X from 1 hour prior to through 4 hours post LPS challenge. At both challenge doses of endotoxin, the group of mice which received lipid X shortly after endotoxin challenge showed higher mortality than the group on either side. Perhaps this is due to the fact that those animals were anesthetized twice in a short period and received the toxic endotoxin challenge before receiving lipid X. The reversal of the lethal toxicity of endotoxin at times as late as 4 hours after endotoxin challenge is especially striking. Although this was best demonstrated at the lower endotoxin dose of 250 μg per mouse, this still represents a massive challenge (approximately 10 mg of lipopolysaccharide per body weight). By 4 hours after injection of the 250 μg of intravenous lipopolysaccharide, the mice had stopped normal behavior, i.e. nesting had stopped, decreased spontaneous activity occurred, and the animals were shaking.

Protection of sheep by lipid X against the lethal toxicity of lipopolysaccharide.

As noted above, the $LD_{50}$ of lipopolysaccharide in sheep is in the vicinity of 10–20 μg/kg, injected intravenously. Sheep respond to lipopoly-saccharide in a manner that more closely resembles the situation encountered in human diseases.

As reported by Burhop (supra), lipid X by itself (40–1000 μg/kg) does not create marked illness or fever. A period of transient pulmonary hypertension and slight short ness of breath subsides after 30 minutes. About 30 sheep were examined by Burhop with regard to lipid X toxicity.

In contrast to lipid X, a single injection of lipopolysaccharide (10–20 μg/kg) causes more serious pulmonary hypertension, and after 15–30 minutes, an animal treated with lipopolysaccharide will begin to tremble, cough and lay down. The symptoms become more severe over the next few hours and are accompanied by fever. About half the animals die by 24 hours.

In view of the partial protection afforded by lipid X against LPS-induced lethality in mice, the possibility of such protection was also examined in sheep. The results are summarized in Table III. The sheep system has the important advantage of permitting the administration of much larger doses of lipid X relative to LPS. It is the ratio of lipid X to endotoxin that is critical for survival. As shown in Table III, all the sheep receiving 100-200 μg/kg of lipid X during the pretreatment period survived subsequent LPS challenge. It is evident that a 5-10 fold excess of lipid X (on a weight basis) over LPS is required to ensure survival. (Because of the inherent LPS resistance of mice, their small body volume, and the limited solubility of lipid X in water, it is impossible to achieve 5-10 fold excess of lipid X relative to LPS in the mouse system.)

In addition to rescuing sheep from lethal effects of LPS, pretreatment with lipid X also alleviates some of the serious clinical symptoms, including shortness of breath, weakness, diarrhea, etc. However, lipid X does not prevent pulmonary hypertension or fever induced by LPS.

Implications for therapy.

Previous work on the lethal endotoxicity of gram-negative lipopolysaccharide showed that limited prevention of the complications of injection of this material could be achieved through the administration of glucocorticoids, prostaglandins, naloxone, pressors, fluid replacement therapy or anti-LPS antibodies. The possibility of using a lipid A fragment, such as lipid X, as an endotoxin antagonist was not considered. In addition, all existing therapies against LPS lethality are dependent upon their being given prior to or very shortly after the administration of the LPS challenge. In the mouse lipid X appears to prevent lethal endotoxicity even when given 4 hours after lipopolysaccharide.

The acute protection afforded by lipid X may have some relationship to the biological phenomenon of lipopolysaccharide tolerance described in the clinical literature. However, lipid X-induced protection against lipopolysaccharide is immediate and wears off after several hours, whereas classical tolerance does not appear for many days and may, in part, be mediated by antibodies.

It is anticipated that administration of lipid X may ameliorate pathological conditions created by many of the endotoxin-induced diseases listed in Table I. Furthermore, protection by lipid X can be obtained even after endotoxin had been administered. This is a unique and extremely important therapeutic consideration, since the signs and symptoms of a disease are almost always manifest before therapy is initiated. Although the mechanism(s) of protection by lipid X against lipopolysaccharide challenge remain unknown, the data fit best with competition for a common target molecule, such as membrane receptor(s) on endothelial or vascular cells. The action of lipid X is much too fast to have an immunological cause.

Because lipid X by itself is not seriously toxic to animals, it may be useful for treatment of other diseases which lipopolysaccharide is known to ameliorate, but cannot be employed because of its toxicity. Thus, it might be anticipated that lipid X would protect mammals from skatole toxicity, oxygen toxicity, and drugs that enhance the production of free radicals (e.g. bleomycin, nitrofurantoin, adriamycin, etc.). It is known that LPS stimulates the activity of various enzymes that protect animals against oxidant stresses, and it can be anticipated that lipid X will have these beneficial effects as well.

Because lipid X is chemically defined and highly purified, it will be a very valuable agent with which to standardize the Limulus amebocyte lysate assay, a widely used test for endotoxin. Endotoxin per se is not a good standard because it is not chemically defined or chemically homogeneous.

The compound lipid X and its various modified derivatives possessing lipid X activity may be introduced into the circulation of an animal by intravenous, intraperitoneal or intramuscular routes, and appear to induce a state of relative resistance to the deleterious effect of lipopolysaccharide When thus employed, lipid X and related compounds may be administered in the form of parenteral solutions containing the selected protective compound, in a sterile liquid suitable for intravenous or other administration. The exact route, dose, and administration interval of the active compound will vary with the size and weight of the animal, and the species, and the desired level of protection.

TABLE I

Pet Animal and Livestock Endotoxemias and Other Pathophysiological Entities with High Probability of Being Prevented or Treated by Administration of Lipid X or Compounds Having Lipid X Activity are the following:

Mammalian

Gastritis
Digestive disorders of the rumen including-
Bloat
Simple indigestion
Grain overload
Abomasal disorders
Displacement/torsion of the abomasum
Impaction of the abomasum
Edema disease of swine
Colibacillosis of weaned pigs
Enteritis of small and large animals
Small intestinal obstruction
Colon impaction of small animals
Intussuceptions
Intestinal torsion and volvulus
Impaction of the large intestine
Intestinal foreign bodies
Intestinal incarceration
Colitis
Colic in horses
Salmonellosis/typhoid fever
Colibacillosis
Diarrhea of newborn animals
Chronic diarrhea
Toxicosis of chemical and plant origins
Gastrointestinal parasites including coccidiosis and sarcosporidiosis
Malabosorbtion syndrome
Hemorrhagic bowel syndrome
All other syndromes which cause loss of gastrointestinal hemogeneity such as abrupt changes in diet or feeding regimen in mammalian species.
Infectious necrotic hepatitis
Bacillary hemoglobinuria
Hepatitis of parasitic etiology
Hepatic distomatosis
Chemical hepatosis from protein deficiencies, vitamin E deficiency, pyrrolizidine alkaloids, from parasites during migrations, infectious and pyogenic diseases, metabolic diseases, copper poisonings.
Avian syndromes
Enteritis of infectious or nutritional origin; infectious etiology is intended to include bacterial, viral and parasitic etiologies.
Hepatitis of infectious or parasitic etiologies
Coccidiosis, hexamitiasis, histomoniasis

TABLE II

Human Diseases with High Probability of Being Prevented or Treated by the Administration of Lipid X or Compounds Having Lipid X Activity are the following (1) Gram-negative sepsis

TABLE II-continued

Human Diseases with High Probability of Being Prevented or Treated by the Administration of Lipid X or Compounds Having Lipid X Activity are the following (2) Endotoxemia from burn wounds, pyelonephritis, peritonitis, cellulitis, abscess, prostatitis, genitourinary tract infections, mastitis, pneumonia, empyema, cholecystitis, bacterial hepatitis, meningococcemia, gonococcemia, colitis, toxic megacolon, etc.
(3) Loss of G.I. mucosal barrier, e.g. trauma, drug-induced mucositis.

TABLE III

Lipid X Protects Sheep Against the Lethal Effects of Intravenous Lipopolysaccharide

| Number of Sheep | Dose of Lipid X ($\mu$g/kg) | Dose of Lipopolysaccharide ($\mu$g/kg) | Survivors |
|---|---|---|---|
| 3 | 0 | 10 | 2/3 |
| 8 | 0 | 20 | 4/8 |
| 3 | 200[a] | 20 | 3/3 |
| 3 | 100[b] | 10 | 3/3 |
| 4 | 100[a] | 20 | 4/4 |
| 2 | 50[a] | 20 | 1/2 |

[a] Administered 1 hour prior to endotoxin.
[b] Administered 15 min. prior to endotoxin.

REFERENCES

1. Raetz, C.R.H., Purcell, S., and Takayama, K. (1983) Proc. Natl. Acad. Sci. USA 80, 4624–4628.
2. Weinberg, J.B., Chapman, H.A., Jr., and Hibbs, J.B., Jr. (1978) J. Immunol. 121, 72–80.
3. Ribi, E.E., Granger, D.L., Milner, K.C., and Strain, S.M. (1975) J. Natl. Cancer Inst. 55, 1253–1257.
4. Ribi, E.E., Cantrell, J.L., Von Eschen, K.B., and Schwartzman, S. (1979) Cancer Res. 39, 4756–4759.
5. Snapper, J.R., Bernard, G.R., Hinson, J.M., Jr., Hutchison, A.A., Loyd, J.E., Ogletree, M.L., and Brigham, K.L. (1983) Am. Rev. Respir. Dis. 127, 306–309.
6. Brigham, K.L., Bowers, R.E., and Haynes, J. (1979) Cir. Res. 45(2), 292–297.
7. Kashtan, J., Blaisdell, F.W., Lin, H.J., and Zaiss, C. (1982) Adv. Schock Res. 7, 173–177.
8. Galanos, C., Rietschel, E.Th., Luderitz, O., Westphal, O., Kim, Y.B., and Watson, D.W. (1972) Eur. J. Biochem. 31, 230–233.
9. Takayama, K., Qureshi, N., Mascagni, P., Nashed, M.A., Anderson, L., and Raetz, C.R.H (1983) J. Biol. Chem. 258, 7379–7385.
10. Raetz, C.R.H. (1984) Rev. Infect. Dis. 6, 463–471.
11. Bulawa, C.E., and Raetz, C.R.H. (1984) J. Biol. Chem. 259, 4846–4851.
12 Ray, B.L., Painter, G., and Raetz, C.R.H. (1984) J. Biol. Chem. 259, 4852–4859.
13. Nishijima, M., Amano, F., Akamatsu, Y., Akagawa, K., Tokunaga, T., and Raetz, C.R.H. Proc. Natl. Acad. Sci. USA, in press (1985).
14. Burhop, K.E., Proctor, R.A., Helgerson, R.B., Raetz, C.R.H., Starling, J.R., and Will, J.A. Am. J. Physiol., submitted.
15. Wightman, P.D., and Raetz, C.R.H. (1984) J. Biol. Chem. 259, 10048–10052.
16. Takayama, K., Qureshi, N., Raetz, C.R.H., Ribi, E., Peterson, J., Cantrell, J.L., Pearson, F.C., Wiggins, J., and Johnson, A.G. (1984) Infect. Immun. 45, 350–355.
17. Proctor, R.A., Will, J.A., Burhop, K.E., and Raetz, C.R.H. Science, submitted.
18. Burhop, K.E. "Pulmonary Pathophysiology in Sheep of Several E. coli Lipid A Precursors." Dissertation submitted to the University of Wisconsin-Madison; Aug. 1984.
19. Golenbock, D., Will, J.A., Raetz, C.R.H., and Proctor, R.A. American Federation for Clinical Research, Abstract, in press, Apr. 1985.

We claim:

1. A method of protecting a mammal from the toxic effects of gram-negative endotoxin which comprises administering by injection to said mammal a safe amount of lipid X which is effective to protect said mammals from said toxic effects.

* * * * *